United States Patent

Widdig et al.

[11] 3,971,804
[45] July 27, 1976

[54] BIS-TRIFLUORO METHYL-IMINO-IMIDAZOLONES

[75] Inventors: Arno Widdig, Blecher; Ingeborg Hammann, Cologne; Helmut Kaspers, Leverkusen, all of Germany

[73] Assignee: Bayer Aktiengesellschaft, Leverkusen, Germany

[22] Filed: Jan. 21, 1975

[21] Appl. No.: 542,885

[30] Foreign Application Priority Data

Jan. 24, 1974 Germany............................ 2403224

[52] U.S. Cl............................. 260/309.7; 424/273
[51] Int. Cl.$^2$........................................... C07D 49/34
[58] Field of Search.................................. 260/309.7

[56] References Cited
UNITED STATES PATENTS 3,459,766  8/1969  Middleton..................... 260/309.6
3,787,435  1/1974  Scholl et al.................. 260/309.7 X

OTHER PUBLICATIONS

Ogden et al., J.A.C.S. 89,5007–89,5009 pertinent (1967).

*Primary Examiner*—Ethel G. Love
*Attorney, Agent, or Firm*—Burgess, Dinklage & Sprung

[57] ABSTRACT

Bis-trifluoromethyl-imino-imidazolones of the formula

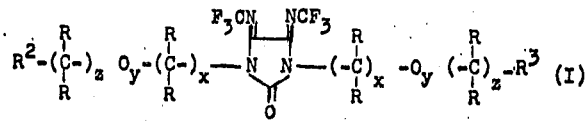

in which
each R independently is hydrogen or methyl,
$R^2$ is a radical selected from the group consisting of bridged rings; fused rings; directly linearly linked rings; rings linked through oxygen, alkylene, oxyalkylene or alkylenoxyalkylene; and substitution products of any of the foregoing with halogen, alkyl or alkoxy with 1 to 4 carbon atoms; said radicals comprising at least two carbon rings, at least one of which is non-aromatic;
$R^3$ is hydrogen or a radical selected from the group consisting of alkyl, alkenyl or alkynyl with up to 8 carbon atoms; substitution products of any of the foregoing with halogen or alkoxy with 1 to 4 carbon atoms; cycloalkyl; cycloalkyl substituted by alkyl with 1 to 4 carbon atoms; aralkyl with up to 4 carbon atoms in the alkyl part; aryl with up to 14 carbon atoms; substitution products of these aralkyl and aryl radicals with halogen, alkyl, haloalkyl or alkoxy with 1 to 4 carbon atoms; and any of the radicals listed under $R^2$;
each $x$ independently is an integer from 0 to 4,
each $y$ independently is 0 or 1 except that $y$ must be 0 if $x$ is 0, and
each $z$ independently is an integer from 0 to 4, which possess acaricidal, insecticidal and fungicidal properties.

14 Claims, No Drawings

BIS-TRIFLUORO METHYL-IMINO-IMIDAZOLONES

The present invention relates to and has for its objects the provision of particular new bis-trifluoromethyl-imino-imidazolones, i.e. 1-tetrahydronaphthyl-, -cyclohexylphenyl-, -cyclohexenylphenyl-, -cyclohexylbenzyl-, -dihydrophenanthryl-, -norbornyl-, or -bicyclohexyl-3-alkyl-, -alkoxyalkyl-, -phenyl-, -cycloalkyl- or -benzyl-4,5-bis-trifluoromethyl-imino-imidazol-2-ones, active compositions in the form of mixtures of such compounds with solid and liquid dispersible carrier vehicles, and methods for producing such compounds and for using such compounds in a new way especially for combating pests, e.g. acarids, insects and fungi, with other and further objects becoming apparent from a study of the within specification and accompanying examples.

Some bis-trifluoromethyl-imino-imidazolones with acaricidal, insecticidal and fungicidal properties have been disclosed in German Published Specification DOS 2,062,346. However, their fungicidal action is not always satisfactory, particularly when used on an industrial scale.

In German Published Specification DAS No. 1,169,194 3-(N,N'-dimethylamino-methyleneimino)-phenylmethylcarbamate is used to combat plant-pathogenic mites. However, its action is not entirely satisfactory.

German Patent Specification No. 836,349 discloses using 0,0-dimethyl-S-(2-ethylmercaptoethyl)-thiophosphoric acid ester for combating insects, but its action is not always satisfactory.

Zinc ethylene-bis-dithiocarbamate is employed extensively for combating plant-pathogenic fungi, but its action is also not always satisfactory.

The present invention provides, as new compounds, the bis-trifluoromethyl-imino-imidazolonnes of the general formula

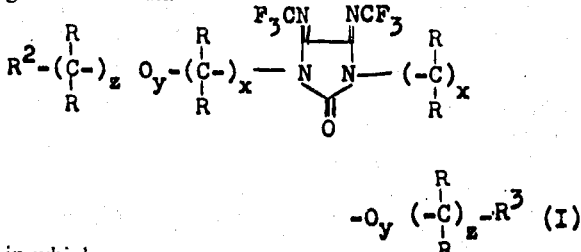

in which
each R independently is hydrogen or methyl,
R² is a radical selected from the group consisting of bridged rings; fused rings; directly linearly linked rings; rings linked through oxygen, alkylene, oxyalkylene or alkylenoxy-alkylene; and substitution products of any of the foregoing with halogen, alkyl or alkoxy with 1 to 4 carbon atoms; said radicals comprising at least two carbon rings, at least one of which is non-aromatic;
R³ is hydrogen or a radical selected from the group consisting of alkyl, alkenyl or alkynyl with up to 8 carbon atoms; substitution products of any of the foregoing with halogen or alkoxy with 1 to 4 carbon atoms; cycloalkyl; cycloalkyl substituted by alkyl with 1 to 4 carbon atoms; aralkyl with up to 4 carbon atoms in the alkyl part; hydrocarbon aryl with up to 14 carbon atoms; substitution products of these aralkyl and aryl radicals with halogen, alkyl, haloalkyl or alkoxy with 1 to 4 carbon atoms; and any of the radicals listed under R²;
each x independently is an integer from 0 to 4,
each y independently is 0 or 1 except that y must be 0 if x is 0, and
each z independently is an integer from 0 to 4.

Those compounds are preferred wherein R² is a bicyclic or tricyclic system in which, in the case of a fused type or a type which has linear linkages, optionally via bridge members, the non-aromatic rings preferably having 5 to 7 ring members and optionally up to 2 double bonds, and substitution products with chlorine, bromine, alkyl and alkoxy with 1 to 4 carbon atoms thereof.

In the case of the bridged hydrocarbon ring types, ring systems with cycloaliphatic rings, of which the number of ring members is 3 to 8 and which can optionally contain up to 2 double bonds, are preferred. In particular, the following types of rings should be mentioned: bicycloheptanes like bicyclo-[1,1,3[-heptane, bicyclo-[1,2,2]-heptane, bicyclooctanes like bicyclo-[1,2,3]-octane, bicyclo-[0,3,3]-octane, bicyclo-[2,2,2]-octane, bicyclononanes like bicyclo-[1,3,3]-nonane, bicyclo-[2,2,3]-nonane, 4,7-methylene-octahydroindene, 1,4-methylene-decahydronaphtalene, 1.4-ethylene-decahydronaphthalene, tricylene and adamantane. These systems can each optionally be monosubstituted or polysubstituted by alkyl and alkoxy with 1 to 4 carbon atoms and by halogen, preferably chlorine and bromine, and can contain up to 2 double bonds. The systems [1,2,2]-bicycloheptane, [1,2,3]-bicyclooctane and tricylene are especially preferred.

In the case of the fused hydrocarbon ring systems, especially preferred compounds are those which contain the basic skeleton of indane, polyhydroindanes like hexahydroindane, polyhydronaphthalenes like tetrahydronaphthalene, decahydronaphthalene, acenaphthene, polyhydroacenaphthenes like tetrahydroacenaphthene, decahydroacenaphthene, polyhydrophenanthrene like dihydrophenanthrene, octahydrophenanthrene, tetradecahydrophenanthrene, polyhydroanthracenes like dihydroanthracene, octahydroanthracene, tetradecahydroanthracene, fluorene or polyhydrofluorenes like hexahydrofluorene. Compounds derived from indane, tetrahydronaphthalene and acenaphthene have proved particularly active.

If the radical R² is a linearly linked hydrocarbon ring system, the following are preferred: cyclopentylbenzene, cyclohexylbenzene, bicyclohexyl, tetrahydrobiphenyl, bicyclopentyl, cyclopentylcyclohexane, polyhyrodiphenylmethanes like hexahydrodiphenylmethane, tetrahydrodiphenylmethane, dodecahydrodiphenylmethane, polyhydrodiphenylethanes like hexahydrodiphenylethane, tetrahydrodiphenylethane, dodecahydrodiphenylethane, polyhydrodiphenyl ethers like hexahydrodiphenyl ether, cyclopentoxybenzene, benzyl cyclohexyl ether, benzyl cyclopentyl ether, polyhydrobenzyl cyclohexyl ethers like hexahydrobenzyl cyclohexyl ether, polyhydrobenzyl-cyclopentyl ethers like hexahydrobenzyl cyclopentyl ether, polyhydrobenzyl-benzyl ethers like hexahydrobenzyl benzyl ether, dihexahydrophenylethyl cyclohexyl ether and hexahydrobenzyl phenyl ether. Compounds which possess the following ring systems of the linearly linked type are here particularly preferred: cyclohexylbenzene, tetrahydrodiphenyl, bicyclohexyl, hexahydrodiphenylmethane and dodecahydrodiphenylmethane.

The linearly bridged systems are preferably bridged to one another direct or via oxygen or via alkylene bridges with up to 4 carbon atoms, which are optionally interrupted by an oxygen atom. Methylene, ethylene, oxyethylene and oxypropylene bridges, and a direct linkage, are preferred.

$R^3$ is preferably hydrogen or alkyl, alkenyl or alkynyl with up to 6 carbon atoms optionally substituted by chlorine, methoxy or ethoxy (especially methyl, ethyl, n-propyl, isopropyl, n-butyl, iso-butyl, tert.-butyl, amyl, hexyl, 2-methoxyethyl, 2-ethoxyethyl, 3-methoxypropyl, 3-ethoxypropyl, 2-chloroethyl, allyl and propargyl), or optionally methyl-substituted cycloalkyl with 5 to 7 carbon atoms (especially cyclopentyl, cyclohexyl, cycloheptyl, 2-methylcyclohexyl, 3-methylcyclohexyl and 4-methylcyclohexyl), or optionally chlorine-substituted or methoxy-substituted aralkyl (especially benzyl and phenylethyl), or optionally chlorine-substituted, methyl-substituted or methoxy-substituted aryl (especially phenyl).

The compounds according to the invention possess a substantially better fungicidal activity than the compounds known from German Published Specification DOS No. 2,062,346, and than zinc ethylene-bis-dithiocarbamate.

Furthermore, they have a far better acaricidal activity than 3-(N,N'-dimethylamino-methyleneimino)-phenylmethylcarbamate, an active compound used in the art for combating plant-pathogenic mites. They also have a far better insecticidal activity than O,O'-dimethyl-S-(2-ethylmercaptoethyl)-thiolphosphoric acid ester, an active compound used in the art for combating insects harmful to plants. The better activity of the compounds according to the invention compared to known materials is surprising and they thus represent an enrichment of the art.

The present invention also provides a process for the preparation of a bis-trifluoromethyl-imino-imidazolone of the formula (I) in which a urea of the general formula

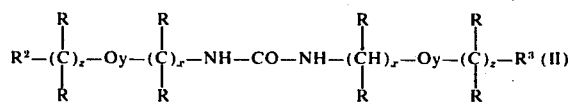

in which
R, $R^2$, $R^3$, x, y and z have the above-mentioned meanings is reacted with perfluoro-2,5-diazahexa-2,4-diene of the formula $$F_3C-N=CF-CF=N-CF_3 \qquad (III)$$

in the presence of a hydrogen fluoride acceptor at a temperature of −50° to +120°C, optionally in the presence of an inert solvent or diluent.

If N-[1-(5,6,7,8-tetrahydro)-naphthyl]-N-methoxyethylurea and perfluoro-2,5-diazahexa-2,4-diene are used as starting materials and sodium fluoride is used as the acid-binding agent, the course of the reaction can be represented by the following equation:

(IIa)

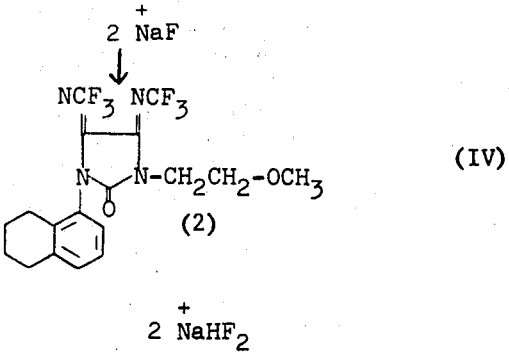

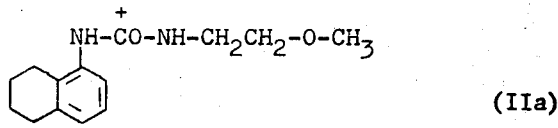

The ureas of the formula (II) used to prepare the compounds according to the invention have, in some cases, been described in the literature or can be prepared in accordance with the processes customary for the preparation of ureas; e.g. Methoden der organischen Chemie (Methods of organic Chemistry), Houben-Weyl, volume VIII, pages 149 to 163, Thieme-Verlag Stuttgart (1952). Preferably, the ureas are prepared from the corresponding isocyanates and amines (ibid., page 157 et seq.).

A number of the amines to be used for the preparation of the above-mentioned ureas have not hitherto been described in the literature. They can be prepared according to known processes. For example, they are obtained by catalytic hydrogenation of the corresponding nitro compounds, by amine substitution of halogen compounds or by amine addition to unsaturated systems, e.g. Houben-Weyl, volume XI/1, pages 24 et seq., 267 et seq. and 360 to 474, Thieme-Verlag Stuttgart (1957).

The perfluoro-2,5-diazahexa-2,4-diene of the formula (III) to be used as a starting material is known, e.g. Journal of the American Chemical Society, volume 89, page 5007 (1967).

The process for the preparation of the compounds according to the invention can be carried out in organic solvents or diluents. These include hydrocarbons, such as benzine, toluene and benzene, nitriles, such as acetonitrile, and chlorinated hydrocarbons, such as methylene chloride, chloroform and chlorobenzene.

The customary acid-binding agents can be used to bind the hydrogen fluoride liberated in the reaction. As such agents it is possible to use alkali metal carbonates, alkali metal bicarbonate or tertiary amines, such as triethylamine or dimethylaniline. However, the alkali metal fluorides, especially sodium fluoride, are preferred as hydrogen fluoride acceptors.

The reaction temperatures can be varied over a fairly wide range. In general, the reaction is carried out at from −50°C to +120°C, preferably at from −30°C to +90°C.

To carry out the process according to the invention, 1 mole of perfluoro-2,5-diazahexa-2,4-diene of the formula (III) is generally employed per mole of urea according to formula (II). The alkali metal fluoride used as a hydrogen fluoride acceptor is generally employed in a 2-molar to 4-molar excess. Ratios which are up to 20 per cent by weight below or above those mentioned can be used without significantly lowering the yield. Preferably, the perfluoro-2,5-diazahexa-2,4-diene is added dropwise to a suspension consisting of urea, organic solvent and hydrogen fluoride acceptor. After completion of the reaction, the fluoride formed is filtered off, the filtrate is concentrated and the crystalline residue is recrystallized. However, it is also possible to add water to the reaction batch after completion of the reaction, filter off the residue produced and recrystallize it if appropriate.

It is particularly advantageous to carry out the preparation of the urea and the subsequent reaction with perfluoro-2,5-diazahexa-2,4-diene in a so-called 'one-pot' reaction. In this case, the amines which are suitable for use as starting compounds are reacted directly with isocyanates in accordance with known processes and the perfluoro-2,5-diazahexa-2,4-diene is added to the resulting reaction solution without isolating the intermediates.

A further variation of the process for the preparation of the compounds according to the invention is to react suitable ureas with a perfluoro-2,5-diazahexa-2,4-diene precursors, e.g. the known compound N,N'-bis-(trifluoromethyl)tetrafluoroethylene-1,2-diamine, in the presence of a hydrogen fluoride acceptor at a temperature of about −50°C to +120°C. In this case, it is advantageous to use about 1 mole of N,N-bis-(trifluoromethyl)-tetrafluoroethylene-1,2-diamine and 4 moles of hydrogen fluoride acceptor per mole of urea. The process is carried out analogously to the method disclosed in German Published Specification DOS No. 2,210,884.

As already mentioned, the compounds according to the invention are highly active acaricides, insecticides and fungicides, without displaying properties harmful to plants at the customary use concentrations. They can therefore be employed particularly advantageously for combating sucking and biting insects, including pests harmful to health and pests of stored products, as well as mites and plant-pathogenic fungi.

Sucking insects contemplated herein include particularly aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (*Lepidoptera*) such as the diamond-black moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (*Coleoptera*), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, *Orthoptera*, for example the house cricket (*Gryllus domesticus*); termites such as the eastern subterranean termite (*Reticulitermes flavipes*) and *Hymenoptera* such as ants, for example the garden ant (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phorbia regina*), the bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acarina*) there are classed, in particular, the spider mites (*Tetranychidae*) such as the two-spotted spider mite (*Tetranychus urticae*) and the European red mite (*Paratetranychus pilosus* = *Panonychus ulmi*), gall mites, for example the black-currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compounds are also distinguished by an outstanding residual activity on wood and clay, as well as good stability to alkali on limed substrates.

The active compounds according to the invention furthermore exhibit a high degree of fungitoxic activity and a broad spectrum of activity and have a relatively low toxicity to warm-blooded animals, as a result of which they are easy to handle and can be employed in practice for combating undesired fungal growth. Their good toleration by plants also permits them to be used against fungal plant diseases by treating the growing crop plant or isolated parts thereof or the seed or the culture soil. The active compounds are particularly active against fungi which cause tracheomycosis and attack the plants through the soil, such as species of Verticillium, species of Fusarium and species of Phialophora. However, they also exhibit a very good action against seed-borne fungi, such as *Tilletia tritici*, *Ustilago avenae*, *Fusarium nivale*, species of Helminthosporium and fungi which inhabit the soil such as species of Rhizoctonia, species of Fusarium, species of Pythium and species of Thielaviopsis.

The active compounds according to the invention can furthermore be used against parasitory fungi on parts of plants which are above the ground. Thus they are active against fungi of the genera Botrytis and Fusicladium.

The active compounds can, however, also be employed with good success for combating other phytopathogenic fungi, for example fungi which cause diseases in rice and horticultural plants, especially *Pircularia oryzae, Pellicularia sasakii, Cochliobolus miyabeanus, Cercospora musae* and *Phialosphora cinerescens.*

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other acaricides, insecticides and fungicides, or bactericides, rodenticides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. acarids, insects and fungi, which comprises applying to at least one of correspondingly (a) such acarids, (b) such insects, (c) such fungi, and (d) the corresponding habitat thereof, i.e. the locus to be protected, e.g. to a growing crop, to an area where a crop is to be grown or to a domestic animal, a correspondingly combative or toxic amount, i.e. an acaricidally, insecticidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained is expressed as a percentage: 100% means that all the spider mites were killed, whereas 0% means that none of the spider mites were killed.

The active compounds, the concentrations of the active compounds, the evaluation times and the results can be seen from the following table:

Table 1

| Active compounds | Active compound concentration in % | Degree of destruction in % after 8 days |
|---|---|---|
| 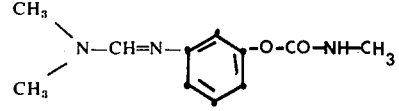 (known) | 0.1<br>0.01 | 95<br>0 |
| (7) 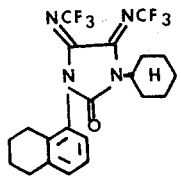 | 0.1<br>0.01 | 100<br>98 |
| (8) 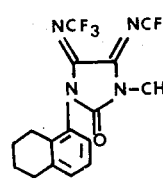 | 0.1<br>0.01 | 100<br>98 |
| (9) 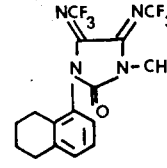 | 0.1<br>0.01 | 98<br>85 |
| (10) 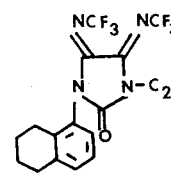 | 0.1<br>0.01 | 100<br>98 |

(Mites which damage plants) *Tetranychus* test

Table 1-continued (Mites which damage plants)
Tetranychus test

| Active compounds | Active compound concentration in % | Degree of destruction in % after 8 days |
|---|---|---|
| (3) [imidazolidinone with N-C$_3$H$_7$, tetrahydronaphthyl, =NCF$_3$, =NCF$_3$] | 0.1<br>0.01 | 100<br>98 |
| (4) [imidazolidinone with N-C$_4$H$_9$, tetrahydronaphthyl, =NCF$_3$, =NCF$_3$] | 0.1<br>0.01 | 100<br>98 |
| (5) [imidazolidinone with N-C$_4$H$_9$-i, tetrahydronaphthyl, =NCF$_3$, =NCF$_3$] | 0.1<br>0.01 | 100<br>80 |
| (6) [imidazolidinone with N-C$_4$H$_9$-t, tetrahydronaphthyl, =NCF$_3$, =NCF$_3$] | 0.1<br>0.01 | 100<br>98 |
| (2) [imidazolidinone with N-CH$_2$-CH$_2$-OCH$_3$, tetrahydronaphthyl, =NCF$_3$, =NCF$_3$] | 0.1<br>0.01 | 100<br>98 |
| (20) [imidazolidinone with N-CH$_3$, tetrahydronaphthyl, =NCF$_3$, =NCF$_3$] | 0.1<br>0.01 | 98<br>95 |

Table 1-continued (Mites which damage plants)
*Tetranychus* test

| Active compounds | Active compound concentration in % | Degree of destruction in % after 8 days |
|---|---|---|
| (21) tetrahydronaphthyl-N,N'-(bis-trifluoromethylimino)imidazolidinone, N'-C₂H₅ | 0.1 / 0.01 | 100 / 98 |
| (13) tetrahydronaphthyl-N,N'-(bis-trifluoromethylimino)imidazolidinone, N'-C₃H₇ | 0.1 / 0.01 | 100 / 98 |
| (14) tetrahydronaphthyl-N,N'-(bis-trifluoromethylimino)imidazolidinone, N'-C₄H₉ | 0.1 / 0.01 | 100 / 98 |
| (15) tetrahydronaphthyl-N,N'-(bis-trifluoromethylimino)imidazolidinone, N'-C₄H₉-i | 0.1 / 0.01 | 98 / 95 |
| (12) tetrahydronaphthyl-N,N'-(bis-trifluoromethylimino)imidazolidinone, N'-CH₂-CH₂-OCH₃ | 0.1 / 0.01 | 100 / 98 |
| (33) tetrahydronaphthyl-N,N'-(bis-trifluoromethylimino)imidazolidinone, N'-CH₃ | 0.1 / 0.01 | 100 / 60 |
| (1) (4-cyclohexylphenyl)-N,N'-(bis-trifluoromethylimino)imidazolidinone, N'-CH₃ | 0.1 / 0.01 | 98 / 80 |
| (23) (4-cyclohexylphenyl)-N,N'-(bis-trifluoromethylimino)imidazolidinone, N'-CH₂-CH₂-OCH₃ | 0.1 / 0.01 | 95 / 80 |

Table 1-continued

| (Mites which damage plants) Tetranychus test Active compounds | | Active compound concentration in % | Degree of destruction in % after 8 days |
|---|---|---|---|
| (28) | 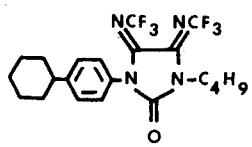 | 0.1<br>0.01 | 98<br>85 |
| (29) | 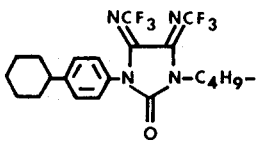 | 0.1<br>0.01 | 100<br>98 |

EXAMPLE 2

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 2

| (Insects which damage plants) Plutella test Active compounds | | Active compound concentration in % | Degree of destruction in % after 3 days |
|---|---|---|---|
| 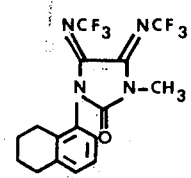<br>(known) | | 0.1<br>0.01 | 100<br>0 |
| (8) | 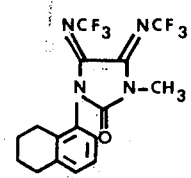 | 0.1<br>0.01 | 100<br>80 |
| (10) | 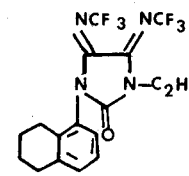 | 0.1<br>0.01 | 100<br>80 |

Table 2-continued (Insects which damage plants)
*Plutella* test

| Active compounds | Active compound concentration in % | Degree of destruction in % after 3 days |
|---|---|---|
| (3) [structure: tetrahydronaphthyl-imidazolidinone with two NCF$_3$ groups, N-C$_3$H$_7$] | 0.1<br>0.01 | 100<br>85 |
| (4) [structure: tetrahydronaphthyl-imidazolidinone with two NCF$_3$ groups, N-C$_4$H$_9$] | 0.1<br>0.01 | 100<br>90 |
| (5) [structure: tetrahydronaphthyl-imidazolidinone with two NCF$_3$ groups, N-C$_4$H$_9$-i] | 0.1<br>0.01 | 100<br>95 |
| (14) [structure: tetrahydronaphthyl-imidazolidinone, N-C$_4$H$_9$] | 0.1<br>0.01 | 100<br>65 |
| (12) [structure: tetrahydronaphthyl-imidazolidinone with two NCF$_3$ groups, N-CH$_2$-CH$_2$-OCH$_3$] | 0.1<br>0.01 | 100<br>65 |

EXAMPLE 3

Fusicladium test (apple scab) (Protective)

Solvent: 4.7 parts by weight of acetone Emulsifier: 0.3 part of weight of alkylaryl polyglycol ether Water: 95.0 parts by weight The amount of active compound required for the desired concentration of the active compound in the spray liquid was mixed with the stated amount of solvent, and the concentrate was diluted with the stated amount of water which contained the stated addition.

Young apple seedlings in the 4 – 6 leaf stage were sprayed with the spray liquid until dripping wet. The plants remained in a greenhouse for 24 hours at 20°C and at a relative atmospheric humidity of 70%. They were then inoculated with an aqueous conidium suspension of the apple scab causative organism (*Fusicladium dendriticum Fuckel*) and incubated for 18 hours in a humidity chamber at 18° – 20°C and at a relative atmospheric humidity of 100%.

The plants were then brought into a greenhouse for 14 days.

15 days after inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table.

Table 3

| Active compound | Fusicladium test / protective Infection in % of the infection of the untreated control at an active-compound concentration (in %) of 0.00062 |
|---|---|
| 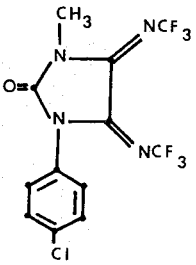<br>(known from German Published Specification) DOS 2,062,346) | 19 |
| (I) 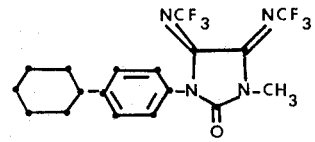 | 0 |

EXAMPLE 4

Podosphaera test (powdery mildew of apples)
[Protective]

Solvent: 4.7 parts by weight of acetone Emulsifier: 0.3 parts by weight of alkylaryl polyglycol ether Water: 95.0 parts by weight The amount of active compound required for the desired concentration of the active compound in the spray liquid was mixed with the stated amount of solvent, and the concentrate was diluted with the stated amount of water which contained the stated addition.

Young apple seedlings in the 4 – 6 leaf stage were sprayed with the spray liquid until dripping wet. The plants remained in a greenhouse for 24 hours at 20°C and at a relative atmospheric humidity of 70%. They were then inoculated by dusting with conidia of the apple powdery mildew causative organism (Podosphaera leucotricha Salm.) and placed in a greenhouse at a temperature of 21°– 23°C and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table 4:

Table 4

| Active compound | Podosphaera test / protective Infection in % of the infection of the untreated control at an active compound concentration (in %) of 0.00125 |
|---|---|
| 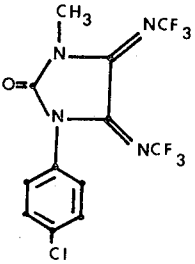<br>(known from German Published Specification) DOS 2,062,346) | 74 |
| (I) 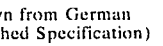 | 2 |

EXAMPLE 5

Mycelium growth test

Nutrient medium used:
  20 parts by weight of agar-agar
  200 parts by weight of potato decoction
  5 parts by weight of malt 15 parts by weight of dextrose
5 parts by weight of peptone
2 parts by weight of Na$_2$HPO$_4$
0.3 part by weight of Ca(NO$_3$)$_2$
Ratio of solvent mixture to nutrient medium:
2 parts by weight of solvent mixture
100 parts by weight of agar nutrient medium
Composition of solvent mixture:
0.19 part by weight of DMF or acetone
0.01 part by weight of emulsifier Emulvin W
1.80 parts by weight of water
2.00 parts by weight of solvent mixture with the growth on the control nutrient media. The fungal growth is rated in terms of the following figures:

```
     1:  no fungal growth
up to 3:  very strong inhibition of growth
up to 5:  medium inhibition of growth
up to 7:  slight inhibition of growth
     9:  growth equal to the untreated control.
```

The active compounds, the active compound concentrations and the results can be seen from the table which follows:

Table 5

Mycelium growth test
Fungi and 1 bacterium

| Active compounds | Active compound concentration, ppm | A | B | C | D | E | F | G | H | I | J | K | L | M | N | O | P | Q |
|---|---|---|---|---|---|---|---|---|---|---|---|---|---|---|---|---|---|---|
| CH$_2$—NH—CS—S\\\\Zn<br>CH$_2$—NH—CS—S// (known) | 10 | 9 | 9 | 9 | 9 | 9 | 5 | 9 | 9 | 9 | 9 | 9 | 5 | 5 | 9 | 9 | 9 | 9 |
| (1) | 10 | 3 | 3 | 5 | 5 | 1 | 1 | 5 | 3 | 5 | 1 | 5 | 1 | 1 | 5 | 1 | 1 | — |
| (12) | 10 | 2 | 3 | 1 | 1 | 1 | 1 | 3 | 5 | 3 | 1 | — | 1 | 1 | 3 | 1 | 1 | — |
| (23) | 10 | 5 | 3 | 3 | 5 | 3 | 3 | 5 | — | 5 | 1 | — | 3 | 1 | — | 1 | 2 | — |
| (2) | 10 | 1 | 1 | 3 | 1 | 1 | 1 | 3 | 5 | 3 | 1 | — | 1 | 1 | 1 | 1 | 1 | — |
| (3) | 10 | 5 | 1 | 5 | — | — | 1 | 5 | — | — | 1 | — | 1 | 1 | 1 | 1 | 1 | — |
| (4) | 10 | 5 | 5 | — | — | — | 5 | 5 | — | — | 1 | — | 1 | 1 | 1 | 1 | — | — |
| (5) | 10 | 5 | 5 | 5 | — | — | 5 | 5 | — | 5 | 3 | — | 1 | 1 | 3 | 1 | 5 | — |
| (7) | 10 | 5 | — | — | — | — | — | 5 | — | — | 1 | — | 3 | 1 | 3 | 1 | — | — |
| (13) | 10 | — | 5 | — | — | — | — | 5 | — | — | — | — | 1 | 1 | 3 | 5 | — | — |
| (14) | 10 | 5 | 1 | 5 | — | — | — | 5 | — | — | 3 | — | 1 | 1 | — | 1 | — | — |
| (16) | 10 | 5 | 5 | — | — | — | 5 | 5 | — | 5 | 3 | — | 1 | 1 | 3 | 1 | 5 | — |
| (18) | 10 | — | — | — | — | — | — | 3 | — | — | 3 | — | 1 | 1 | 3 | 1 | — | 5 |
| (19) | 10 | 5 | — | 5 | — | — | 5 | 5 | — | 5 | 3 | — | 1 | 1 | 3 | 1 | 5 | 5 |
| (20) | 10 | 5 | 3 | — | 3 | — | 3 | 5 | — | — | 1 | — | 1 | 1 | 3 | 3 | 1 | — |
| (8) | 10 | 1 | 1 | 5 | 1 | 5 | 1 | 1 | 3 | 5 | 1 | 3 | 1 | 3 | 1 | 3 | 1 | — |
| (9) | 10 | 5 | 5 | 5 | — | — | — | 3 | — | — | 3 | — | 1 | 1 | 3 | 1 | — | 5 |
| (10) | 10 | 3 | 1 | 3 | 1 | 5 | 1 | 3 | 5 | — | 3 | — | 1 | 1 | 1 | 1 | 1 | — |
| (3) | 10 | — | — | — | — | — | 5 | — | — | 3 | — | 1 | 3 | 5 | 1 | — | 5 | |
| (21) | 10 | 5 | 3 | 5 | 3 | — | 5 | 5 | — | — | 1 | — | 1 | 1 | 5 | 1 | 1 | — |
| (22) | 10 | — | — | 5 | — | — | — | 5 | — | — | 5 | — | 1 | 1 | 1 | 1 | — | — |
| (24) | 10 | — | — | — | — | — | — | — | — | 5 | 1 | — | 1 | 3 | 3 | — | — | — |
| (27) | 10 | — | — | — | — | — | — | — | — | — | 1 | — | 3 | 5 | 1 | 5 | — | — |
| (32) | 10 | — | — | — | 5 | 5 | 5 | 3 | — | 5 | 3 | — | 5 | 5 | 1 | 1 | 5 | — |
| (33) | 10 | 1 | 1 | 2 | 2 | 1 | 1 | 1 | 3 | 5 | 1 | 2 | 1 | 1 | 1 | 1 | 1 | 5 |

A = *Fusarium culmorum*
B = *Sclerotinia sclerotiorum*
C = *Fusarium nivale*
D = *Colletotrichum coffeanum*
E = *Rhizoctonia solani*
F = *Pythium ultimum*
G = *Cochliobolus miyabeanus*
H = *Botrytis cinerea*
I = *Verticillium alboatrum*
J = *Pyricularia oryzae*
K = *Phialophora cinerescens*
L = *Helminthosporium gramineum*
M = *Mycosphaerella musicola*
N = *Phytophthora cactorum*
O = *Venturia inaequalis*
P = *Pellicularia sasakii*
Q = *Xanthomonas oryzae*

The amount of active compound required for the desired concentration of active compound in the nutrient medium was mixed with the stated amount of the solvent mixture. The concentrate was thoroughly mixed, in the stated proportion, with the liquid nutrient medium which had been cooled to 42°C and was then poured into Petri dishes of 9 cm diameter. Control plates to which the active-compound preparation had not been added were also set up.

When the nutrient medium had cooled and solidified, the plates were inoculated with the species of fungi stated in the table and incubated at about 21°C.

Evaluation was carried out after 4 – 10 days, dependent upon the speed of growth of the fungi. When evaluation was carried out, the radial growth of the mycelium on the treated nutrient media was compared

EXAMPLE 6

Seed-dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days of 10°C in a refrigerator.

The germination of the spores on the wheat grains, each of which was contaminated with about 100,000 spores, was subsequently determined microscopically. The smaller the number of spores which had germinated, the more effective was the active compound.

The active compounds, the concentrations of the active compounds in the dressing, the amounts of dressing used and the percentage spore germination can be seen from the following table 6:

mixture with the desired concentration of active compound.

To apply the dressing, rye seed, which was naturally infected by *Fusarium nivale*, was shaken with the dressing in a closed glass flask. Two batches of 100 grains of this seed were sown 1 cm deep in seed boxes containing Fruhstorfer standard soil. The young plants developed in climatic chambers at 10°C, at a relative atmospheric humidity of 95% and in diffused natural light; they showed the typical symptoms of snow mold within the first 3 weeks.

Table 6

Seed dressing test /bunt of wheat

| Active compounds | Active compound concentration in the dressing in % by weight | Amount of dressing in g/kg of seed | Spore germination in % |
| --- | --- | --- | --- |
| without dressing | — | — | 10 |
| CH₂—NH—CS—S\\Zn / CH₂—NH—CS—S (known) | 20 | 2 | 5 |
| (8) [structure with NCF₃, NCF₃, N-CH₃] | 10 | 1 | 0 |
|  | 5 | 1 | 0 |
|  | 2.5 | 1 | 0.5 |
| [structure with NCF₃, NCF₃, N-CH₂-CH₂-OCH₃] (2) | 10 | 1 | 0.5 |

EXAMPLE 7

Seed dressing test/snow mold (seed-borne mycosis)

To produce a suitable dry dressing, the active compound was extended with a mixture of equal parts by weight of talc and kieselguhr to give a finely powdered After this time, the number of Fusarium-infected plants was determined as a percentage of the total number of emerged plants. The smaller the number of diseased plants, the more effective was the active compound.

The active compounds, the concentrations of the active compounds in the dressing, the amounts of dressing used and the number of diseased plants can be seen from the following table:

Table 7

| Active compound | Seed dressing test / snow mould Active compound concentration in the dressing in % by weight | Amount of dressing used in g/kg of seed | Number of plants with *Fusarium* disease, in % of the total number of plants emerged |
| --- | --- | --- | --- |
| without dressing | — | — | 16.4 |
| CH₂—NH—CS\\Zn / CH₂—NH—CS (known) | 30 | 2 | 9.1 |
| (10) | 25 | 2 | 1.6 |

EXAMPLE 8

Shoot treatment test/cereal rust (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20°C and 100% relative atmospheric humidity.

After 10 days' dwell time of the plants at a temperature of 20°C and 80–90% atmospheric humidity, the occurrence of rust pustules on the plant was evaluated. The degree of infection was expressed as a percentage of the infection of the untreated control plants. 0% denotes no infection and 100% denotes the same degree of infection as in the case of the untreated control. The more active the compound, the lower the degree of rust infection.

The active compounds, active-compound concentrations in the spray liquor and degrees of infection can be seen from the table which follows:

Table 8

| Active compounds | | Shoot treatment test/cereal rust/protective Active compound concentration in the spray liquor in % by weight | Infection in % of the untreated control |
|---|---|---|---|
| untreated | | — | 100 |
| (12) | 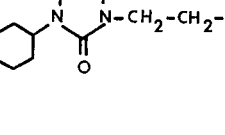 | 0.025<br>0.01 | 0.0<br>32.5 |
| (3) | 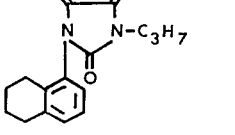 | 0.025<br>0.01<br>0.005<br>0.0025 | 0.0<br>0.0<br>7.5<br>32.5 |
| (4) | 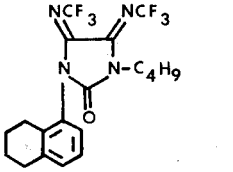 | 0.025 | 0.0 |
| (5) | 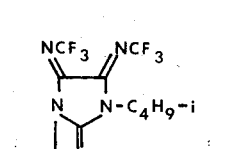 | 0.025 | 50.0 |
| (6) | 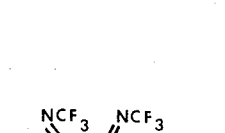 | 0.025 | 18.8 |

Table 8-continued

Shoot treatment test/cereal rust/protective

| Active compounds | Active compound concentration in the spray liquor in % by weight | Infection in % of the untreated control |
|---|---|---|
| (23) [4-cyclohexylphenyl-N, N'-CH$_2$CH$_2$-OCH$_3$, NCF$_3$/NCF$_3$ imidazolidinone] | 0.025<br>0.01 | 18.8<br>37.5 |
| (13) [tetrahydronaphthyl-N, N'-C$_3$H$_7$, NCF$_3$/NCF$_3$ imidazolidinone] | 0.025<br>0.01 | 18.8<br>25.0 |
| (14) [tetrahydronaphthyl-N, N'-C$_4$H$_9$, NCF$_3$/NCF$_3$ imidazolidinone] | 0.025<br>0.01 | 18.8<br>37.5 |
| (15) [tetrahydronaphthyl-N, N'-C$_4$H$_9$-i, NCF$_3$/NCF$_3$ imidazolidinone] | 0.01<br>0.005<br>0.0025 | 0.0<br>6.3<br>21.3 |
| (18) [tetrahydronaphthyl-N, N'-phenyl, NCF$_3$/NCF$_3$ imidazolidinone] | 0.025<br>0.01 | 18.8<br>37.5 |
| (19) [tetrahydronaphthyl-N, N'-CH$_2$-phenyl, NCF$_3$/NCF$_3$ imidazolidinone] | 0.025<br>0.01<br>0.005 | 18.8<br>25.0<br>57.5 |
| (20) [tetrahydronaphthyl-N, N'-CH$_3$, NCF$_3$/NCF$_3$ imidazolidinone] | 0.025<br>0.01<br>0.005<br>0.0025 | 0.0<br>0.0<br>6.3<br>21.3 |
| (8) [dihydronaphthyl-N, N'-CH$_3$, NCF$_3$/NCF$_3$ imidazolidinone] | 0.025<br>0.01<br>0.005<br>0.0025 | 0.0<br>15.0<br>15.0<br>15.0 |

Table 8-continued

Shoot treatment test/cereal rust/protective

| Active compounds | Active compound concentration in the spray liquor in % by weight | Infection in % of the untreated control |
|---|---|---|
| (9) [structure: imidazolidinone with two NCF₃ groups, N-CH₂-phenyl, N-tetrahydronaphthyl] | 0.01<br>0.005<br>0.0025 | 15.0<br>21.3<br>27.5 |
| (3) [structure: imidazolidinone with two NCF₃ groups, N-C₃H₇, N-tetrahydronaphthyl] | 0.025 | 37.5 |
| (21) [structure: imidazolidinone with two NCF₃ groups, N-C₂H₅, N-tetrahydronaphthyl] | 0.025<br>0.01<br>0.005 | 0.0<br>0.0<br>6.3 |

EXAMPLE 9

Sheet treatment test/cereal mildew (leaf-destructive mycosis)

To produce a suitable preparation of active compound, 0.25 part by weight of active compound was taken up in 25 parts by weight of dimethylformamide and 0.06 part by weight of an emulsifier, Emulvin W, and then 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei*.

After 6 days' dwell time of the plants at a temperature of 21°–22°C and 80–90% atmospheric humidity, the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower the degree of mildew infection.

The active compounds, active compound concentrations in the spray liquor and degrees of infection can be seen from the table which follows:

Table 9

Shoot treatment test/cereal mildew/protective

| Active compounds | Active compound concentration in the spray liquor in % by weight | Infection in % of the untreated control |
|---|---|---|
| untreated | — | 100.0 |
| CH₂—NH—CS—S<br>   \<br>    Zn<br>   /<br>CH₂—NH—CS—S<br>(known) | 0.025<br>0.01<br>0.005 | 100.0<br>100.0<br>100.0 |
| (12) [structure: imidazolidinone with two NCF₃ groups, N-CH₂-CH₂-OCH₃, N-tetrahydronaphthyl] | 0.025<br>0.01<br>0.005 | 13.8<br>21.3<br>41.3 |

Table 9-continued

Shoot treatment test/cereal mildew/protective

| Active compounds | Active compound concentration in the spray liquor in % by weight | Infection in % of the untreated control |
|---|---|---|
| (23) | 0.025 | 25.0 |
| (7) | 0.025 | 12.5 |
| (13) | 0.025 | 25.0 |
| (20) | 0.025<br>0.01 | 0.0<br>50.0 |
| (8) | 0.025 | 16.3 |
| (21) | 0.025 | 0.0 |

EXAMPLE 10

Piricularia and Pellicularia test

Solvent: 1.9 parts by weight of DMF
Dispersing agent: 0.1 part by weight of alkylaryl polyglycol ether
Water: 98 parts by weight of water The amount of active compound required for the desired concentration in the spray liquor was mixed with the stated amount of the solvent and of the dispersing agent and the concentrate was diluted with the stated amount of water.

2 × 30 rice plants about 2 – 4 weeks old were sprayed with the spray liquor until dripping wet. The plants remained in a greenhouse at temperatures of 22° to 24°C and a relative atmospheric humidity of about 70% until they were dry. Thereafter, some of the plants were inoculated with an aqueous suspension of 100,000 to 200,000 spores/ml of *Piricularia oryzae* and placed in a chamber at 24° to 26°C and 100% relative atmospheric humidity. The other plants were infected with a culture of *Pellicularia sasakii* grown on malt agar and were set up at 28° to 30°C and 100% relative atmospheric humidity.

5 to 8 days after the inoculation, the infection of all the leaves present at the time of inoculation with *Piricularia oryzae* was determined as a percentage of the untreated but also inoculated control plants. In the case of the plants infected with *Pellicularia sasakii*, the infection at the leaf sheaths after the same time was determined, again in relation to the untreated but infected control. 0% denotes no infection and 100% denotes that the infection was exactly as great as in the case of the control plants.

The active compounds, the concentrations of the active compounds and the results can be seen from the table which follows:

Table 10

| Active compound | *Piricularia*(a) and *Pellicularia*(b) test Infection in % of the infection of the untreated control at an active compound concentration of | |
|---|---|---|
| | (a) 0.025% | (b) 0.025% |
| CH₂—NH—CS—S\<br>\|               Zn<br>CH₂—NH—CS—S<br>(known) | 75 | 100 |
| (23) [structure] | — | 0 |
| (2) [structure] | — | 25 |
| (4) [structure] | — | 13 |
| (13) [structure] | — | 25 |
| (19) [structure] | — | 25 |

Table 10-continued
Piricularia(a) and Pellicularia(b) test
| Active compound | Infection in % of the infection of the untreated control at an active compound concentration of | |
|---|---|---|
| | (a) 0.025% | (b) 0.025% |
| (20) 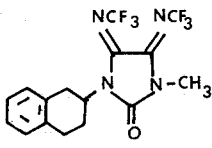 | 25 | — |
| (8) 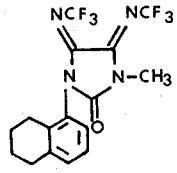 | — | 25 |
| (13) 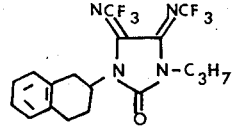 | 13 | — |
| (21) 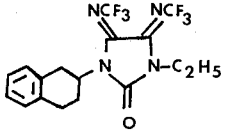 | — | 25 |
| (29) 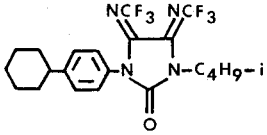 | — | 25 |
| (32) 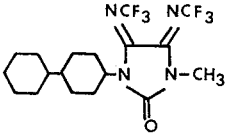 | 25 | 25 |
| (33) 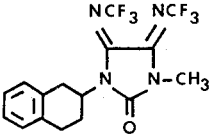 | 0 | 13 |
The process of the present invention is illustrated in the following preparative Examples
EXAMPLE 11
171 g (3 moles) of methylisocyanate were added to

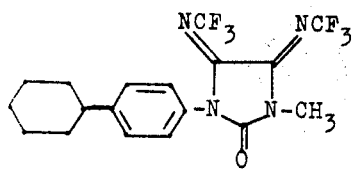 (1)

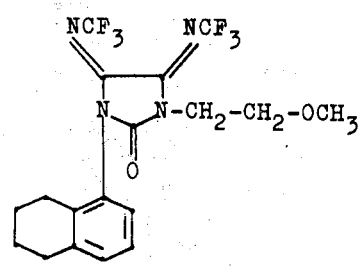 (2)

525 g (3 moles) of p-cyclohexylaniline dissolved in 1.5 liters of dry benzene, while stirring and cooling with ice. The mixture was then brought to the boil for 2 hours, 300 g of sodium fluoride were added and 684 g (3 moles) of perfluoro-2,5-diazahexa-2,4-diene were added dropwise while continuing the boiling. After the addition, the mixture was boiled for a further hour and was filtered hot. The filtrate was concentrated in vacuo and the residue obtained was washed with cold methanol. After drying, 870 g (69% of theory) of product were thus obtained. A sample recrystallized from methanol melted at 155°C.

EXAMPLE 12

375 g (5 moles) of 2-methoxyethylamine were added dropwise to 865 g (5 moles) of α-(5,6,7,8-tetrahydro)-naphthylisocyanate dissolved in 2.5 liters of benzene, while cooling and stirring. After subsequent boiling for 2 hours, 600 g of sodium fluoride and 1,140 g (5 moles) of perfluoro-2,5-diazahexa-2,4-diene were added dropwise while continuing the boiling. After a further hour's boiling, the reaction mixture was filtered hot, the filtrate was concentrated in vacuo and the residue was washed with cold methanol. 1,336 g (61% of theory) of 1-[(5,6,7,8-tetrahydro)-naphthyl]-3-(2-methoxyethyl)-4,5-bis-trifluoromethylimino-imidazol-2-one were obtained. A sample recrystallized from methanol melted at 85°–88°C.

The following compounds can be prepared in a similar manner:

| Formula | Melting point °C, or refractive index |
|---|---|
| (3) 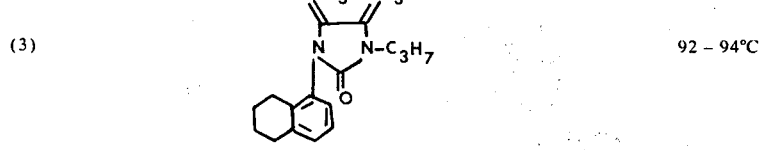 | 92 – 94°C |
| (4) 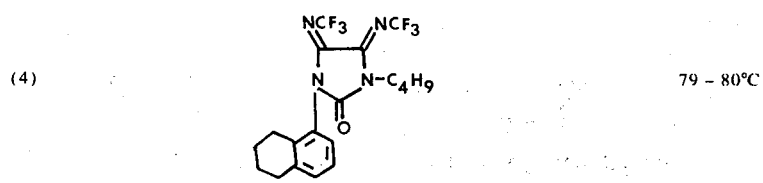 | 79 – 80°C |
| (5) 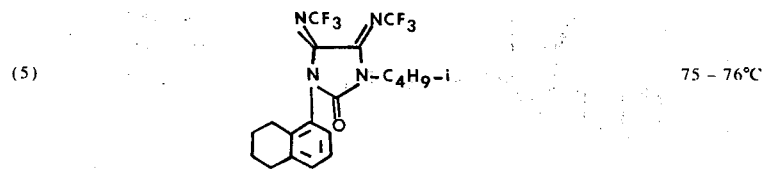 | 75 – 76°C |
| (6) 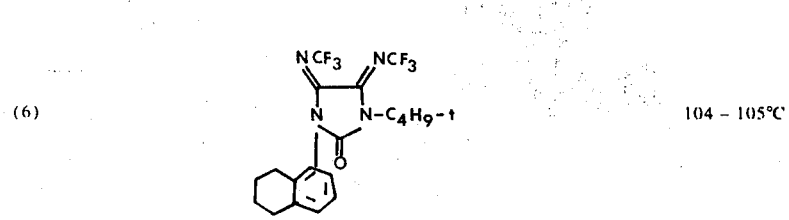 | 104 – 105°C |

-continued
| Formula | | Melting point °C, or refractive index |
|---|---|---|
| (7) | 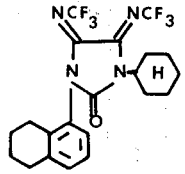 | 131 – 133°C |
| (8) | 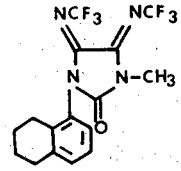 | 124 – 126°C |
| (9) | 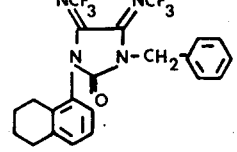 | 99 – 100°C |
| (10) | 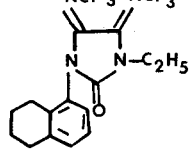 | 129 – 131°C |
| (11) | 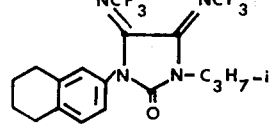 | 139 – 140°C |
| (12) | 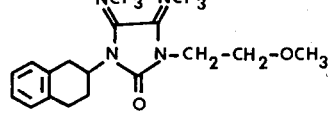 | 74 – 76°C |
| (13) | 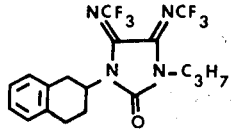 | 91 – 93°C |

-continued
| Formula | | Melting point °C, or refractive index |
|---|---|---|
| (14) | 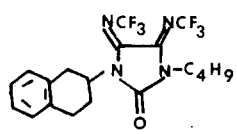 | 80 – 81°C |
| (15) | 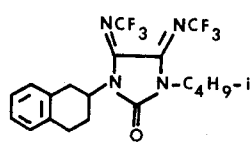 | 93 – 95°C |
| (16) | 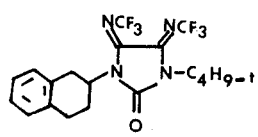 | 109 – 111°C |
| (17) | 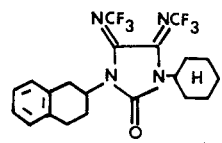 | 160 – 161°C |
| (18) | 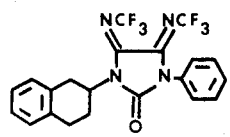 | 152 – 153°C |
| (19) | 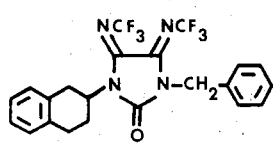 | 96 – 99°C |
| (20) | 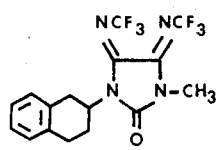 | 126 – 127°C |

-continued
| Formula | | Melting point °C, or refractive index |
|---|---|---|
| (21) | 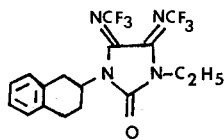 | 107 – 108°C |
| (22) | 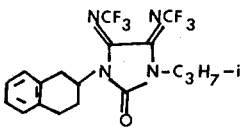 | 128 – 130°C |
| (23) | 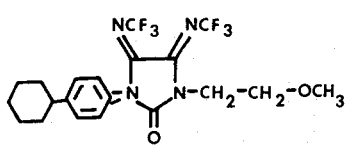 | 105 – 106°C |
| (24) | 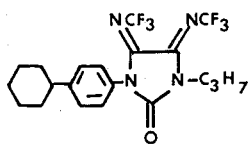 | 101 – 103°C |
| (25) | 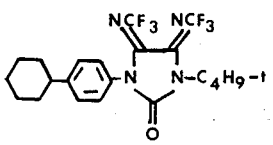 | 128 – 129°C |
| (26) | 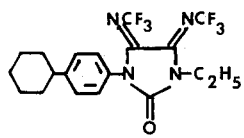 | 160 – 161°C |
| (27) | 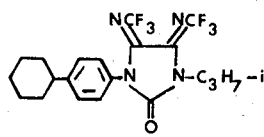 | 127 – 128°C |
| (28) | 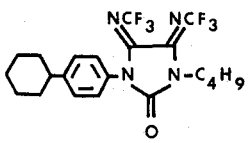 | 104°C |

-continued
| Formula | | Melting point °C, or refractive index |
|---|---|---|
| (29) | 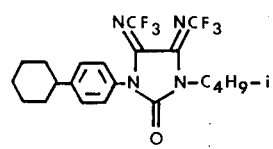 | 87°C |
| (30) | 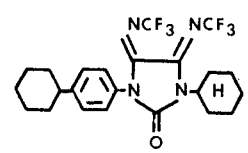 | 160°C |
| (31) | 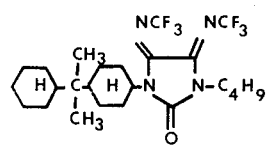 | 91 – 93°C |
| (32) | 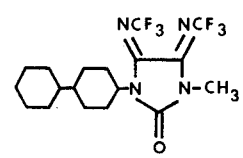 | 126 – 127°C |
| (33) | 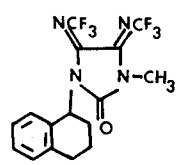 | 134 – 135°C |
| (34) | 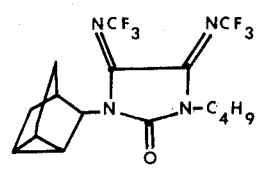 | 54 – 55°C |
| (35) | 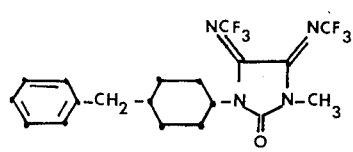 | 92–93°C |

-continued
| Formula | | Melting point °C, or refractive index |
|---|---|---|
| (36) | 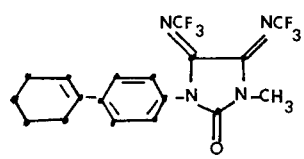 | 164–165°C |
| (37) | 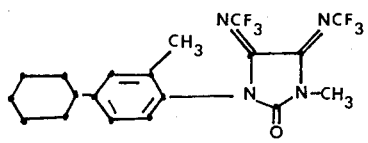 | 130–133°C |
| (38) | 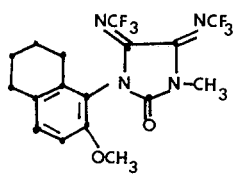 | 112–113°C |
| (39) | 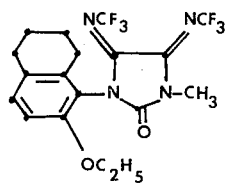 | 93–95°C |
| (40) | 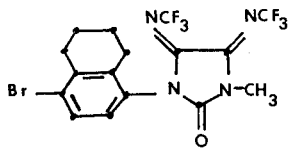 | 152–155°C |
| (41) | 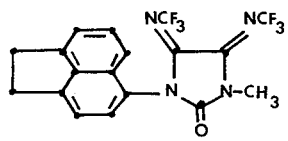 | 168–170°C |
| (42) | 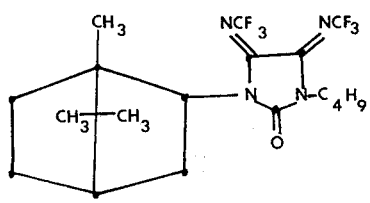 | viscous oil $n_D^{20} = 1.464$ |

-continued
| Formula | Melting point °C, or refractive index |
|---|---|
| (43) 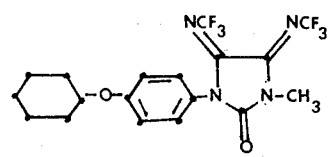 | |
| (44) 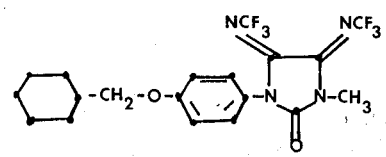 | |
| (45) 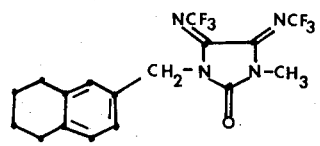 | |
| (46) 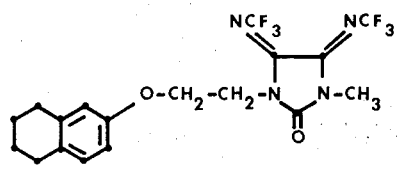 | |
| (47) 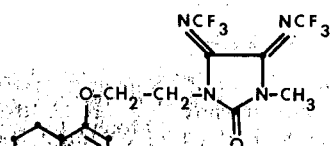 | |
| (48) 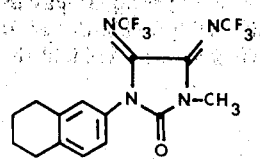 | melting point 167°C |

| Formula | -continued | Melting point °C, or refractive index |
|---|---|---|
| (49) | 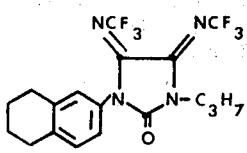 | 100° C |
| (50) | 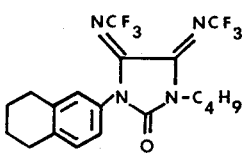 | 123° C |
| (51) | 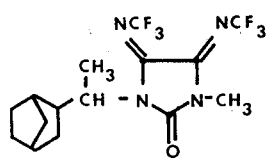 | 100 – 102° C |
| (52) | 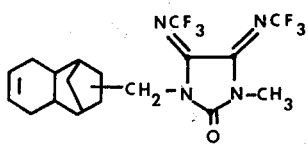 | 98 – 100° C |
| (53) | 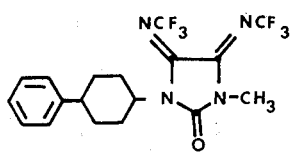 | melting point 93 – 95° C |

It will be appreciated that the instant specification and examples are set forth by way of illustration and not limitation, and that various modifications and changes may be made without departing from the spirit and scope of the present invention.

What is claimed is:

1. A bis-trifluoromethyl-iminoimidazolone of the formula

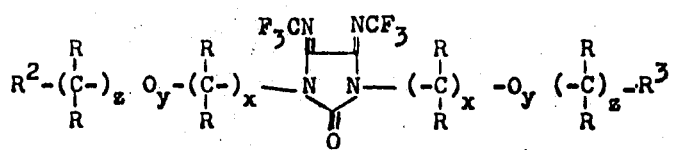

in which
each R independently is hydrogen or methyl,
R² is a radical selected from the group consisting of bridged hydrocarbon rings; fused hydrocarbon rings; directly linearly linked hydrocarbon rings; hydrocarbon rings linked through oxygen, alkylene, oxyalkylene or alkylenoxyalkylene; and substitution products of any of the foregoing with halogen, alkyl or alkoxy with 1 to 4 carbon atoms; said radicals comprising at least two hydrocarbon rings, at least one of which is non-aromatic;
R³ is hydrogen or a radical selected from the group consisting of alkyl, alkenyl or alkynyl with up to 8 carbon atoms; substitution products of any of the foregoing with halogen or alkoxy with 1 to 4 carbon atoms; cycloalkyl with 5 to 7 carbon atoms;

cycloalkyl with 5 to 7 carbon atoms and substituted by alkyl with 1 to 4 carbon atoms; phenylalkyl with up to 4 carbon atoms in the alkyl part; phenyl; substitution products of these phenylalkyl and phenyl radicals with halogen, alkyl, haloalkyl or alkoxy with 1 to 4 carbon atoms; and any of the radicals listed under R²;

each x independently is an integer from 0 to 4, each y independently is 0 or 1 except that y must be 0 if x is 0, and each z independently is an integer from 0 to 4.

2. A compound according to claim 1 in which

R² has two or three carbon rings of which at least one ring is non-aromatic, has 5 to 7 ring members and up to 2 double bonds, R³ is hydrogen or a radical selected from the group consisting of alkyl, alkenyl, alkynyl each with up to 6 carbon atoms and substitution products of the foregoing radicals with chlorine or alkoxy with up to 4 carbon atoms, cyclopentyl, cyclohexyl, cycloheptyl and methyl substitution products thereof; benzyl, chlorobenzyl; methoxybenzyl; phenylethyl; chlorophenylethyl; methoxyphenylethyl; phenyl; chlorophenyl; tolyl, and methoxyphenyl, each x independently is 1 or 2, and each z independently is 0 or 1.

3. A compound according to claim 1 in which

R² is a radical selected from the group consisting of bicycloheptyl, bicyclooctyl, bicyclononyl, 4,7-methyleneoctahydroindenyl, 1,4-methylenedecahydronaphthyl, 1,4-ethylene-decahydronaphthyl, tricyclenyl, adamantyl, indanyl, polyhydroindanyl, polyhydronaphthyl, acenaphthyl, polyhydroacenaphthyl, polyhydrophenanthryl, polyhydroanthracyl, fluorenyl, polyhydrofluorenyl, cyclopentylbenzyl, cyclohexylbenzyl, bicyclohexyl, tetrahydrobiphenyl, bicyclopentyl, cyclopentylcyclohexyl, polyhydrodiphenylmethyl, polyhydrodiphenylethyl, polyhydrodiphenylether, cyclopentoxybenzyl, benzylcyclohexylether, benzylcyclopentylether, polyhydrobenzylcyclohexylether, polyhydrobenzylcyclopentylether, polyhydrobenzyl-benzylether, hexahydrobenzylphenylether, hexahydrobenzylphenylether, tetrahydronaphthylphenylether, -cyclohexylether, -benzylether, -tetrahydrobenzylether, decahydronaphthylphenylether, norbornylphenylether and substitution products of these radicals with chlorine, bromine, alkyl and alkoxy with 1 to 4 carbon atoms.

4. A compound according to claim 1, in which R² is a radical selected from the group consisting of (a) cyclopentylphenyl, cyclohexylphenyl, bicyclohexyl, tetrahydrobiphenyl, bicyclopentyl, cyclopentylcyclohexyl, hexahydrodiphenylmethyl, tetrahydrodiphenylmethyl, dodecahydrodiphenylmethyl, hexahydrodiphenylethyl, tetrahydrodiphenylethyl, dodecahydrodiphenylethyl, hexahydrodiphenyl ether, cyclopentoxyphenyl, benzyl cyclohexyl ether, benzyl cyclopentyl ether, hexahydrobenzyl cyclohexyl ether, hexahydrobenzyl cyclopentyl ether, hexahydrobenzyl benzyl ether, dihexahydrophenylethyl cyclohexyl ether and hexahydrobenzyl phenyl ether, (b) bicyclo-[1,1,3]-heptyl, bicyclo-[1,2,2]-heptyl, bicyclo-[1,2,3]-octyl, bicyclo-[0,3,3,]-octyl, bicyclo-[2,2,2]-octyl, bicyclo-[1,3,3]-nonyl, bicyclo-[2,2,3]-nonyl, 4,7-methyleneoctahydroindenyl, 1,4-methylene-decahydronaphthyl, 1,4-ethylene-decahydronaphthyl, tricylyl, adamantyl, or any of (b) substituted by alkyl or alkoxy with 1 to 4 carbon atoms or halogen, and (c) hexahydroindanyl, decahydronaphthyl, dihydrophenanthryl, octahydrophenanthryl, tetradecahydrophenanthryl, dihydroanthracyl, octahydroanthracyl, tetradecahydroanthracyl, fluorenyl and hexahydrofluorenyl.

5. A compound according to claim 1, in which R² is tetrahydronaphthyl.

6. A compound according to claim 1 wherein such compound is 1 [5,6,7,8-tetrahydro)-naphthyl]-3-propyl)-4,5-bis-trifluoromethylimino-imidazol-2-one of the formula

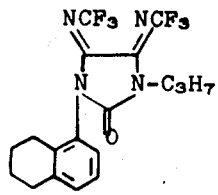

7. A compound according to claim 1 wherein such compound is 1-[(5,6,7,8-tetrahydro)-naphthyl]-3-isobutyl-4,5-bis-trifluoromethylimino-imidazol-2-one of the formula

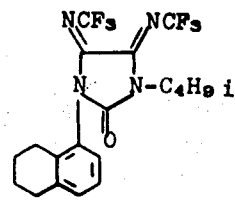

8. a compound according to claim 1 wherein such compound is 1-[(5,6,7,8-tetrahydro)-naphthyl]-3-(2-methoxyethyl)-4,5-bis-trifluoromethyliminoimidazol-2-one of the formula

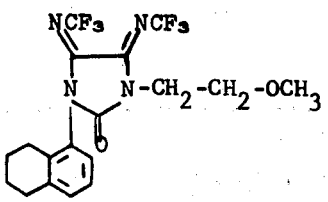

9. A compound according to claim 1 wherein such compound is 2-[(1,2,3,4-tetrahydro)-naphthyl]-3-butyl-4,5-bis-trifluoromethylimino-imidazol-2-one of the formula

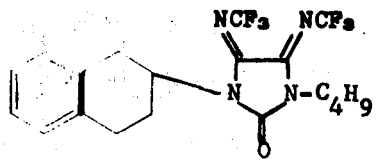

10. A compound according to claim 1 wherein such compound is 2-[(1,2,3,4-tetrahydro)-naphthyl]-3-(2- methoxyethyl)-4,5-bis-trifluoromethylimino-imidazol-2-one of the formula

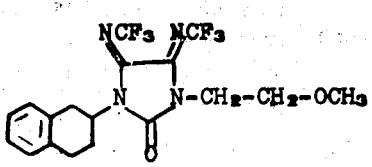

11. A compound according to claim 1 wherein such compound is 1-(4-benzyl-cyclohexyl)-3-methyl-4,5-bis-trifluoromethylimino-imidazol-2-One of the formula

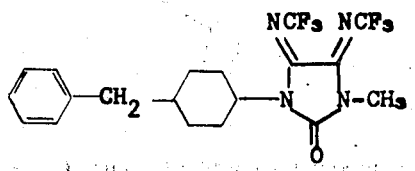

12. A compound according to claim 1 wherein such compound is 1-[2-methoxy-(5,6,7,8-tetrahydro)naphthyl]-3-methyl-4,5-bis-trifluoromethylimino-imidazol-2-one of the formula

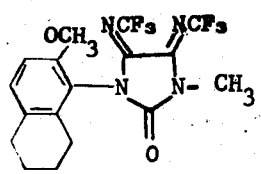

13. A compound according to claim 1 wherein such compound is 1-(4-cyclohexyl)-phenyl-3-(2-methoxyethyl)-4,5-bis-trifluoromethylimino-imidazol-2-one of the formula

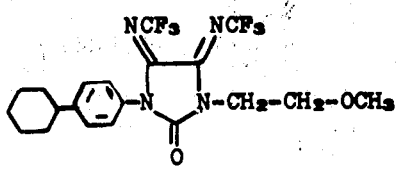

14. A process for the preparation of a bis-trifluoromethyl-imino-imidazolone of the formula

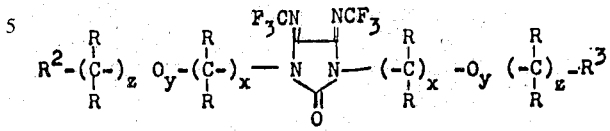

in which
each R independently is hydrogen or methyl,
$R^2$ is a radical selected from the group consisting of bridged hydrocarbon rings; fused hydrocarbon rings; directly linearly linked hydrocarbon rings; hydrocarbon rings linked through oxygen, alkylene, oxyalkylene or alkylenoxyalkylene; and substitution products of any of the foregoing with halogen, alkyl or alkoxy with 1 to 4 carbon atoms; said radicals comprising at least two carbon rings, at least one of which is non-aromatic;
$R^3$ is hydrogen or a radical selected from the group consisting of alkyl, alkenyl or alkynyl with up to 8 carbon atoms; substitution products of any of the foregoing with halogen or alkoxy with 1 to 4 carbon atoms; cycloalkyl with 5 to 7 carbon atoms; cycloalkyl with 5 to 7 carbon atoms and subsituted by alkyl with 1 to 4 carbon atoms; phenylalkyl with up to 4 carbon atoms in the alkyl part; phenyl; substitution products of these phenylalkyl and phenyl radicals with halogen, alkyl, haloalkyl or alkoxy with 1 to 4 carbon atoms,
each $x$ independently is an integer from 0 to 4, each $y$ independently is 0 or 1 except that $y$ must be 0 if $x$ is 0, and
each $z$ independently is an integer from 0 to 4, by mixing a urea of the formula

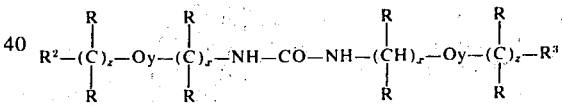

in the presence of a hydrogen fluoride acceptor at a temperature of about −50°C to +120°C with N,N'-bis-(trifluoromethyl)tetrafluoro-ethylene-1,2-diamine which in situ generates perfluoro-2,5-diazahexa-2,4-diene of the formula
which reacts with the urea.

* * * * *